(12) United States Patent
Nakamura et al.

(10) Patent No.: US 12,423,809 B2
(45) Date of Patent: Sep. 23, 2025

(54) MEDICAL IMAGE PROCESSING APPARATUS, METHOD, AND PROGRAM FOR DETECTING ABNORMAL REGION BY SETTING THRESHOLD

(71) Applicant: FUJIFILM Corporation, Tokyo (JP)

(72) Inventors: Keigo Nakamura, Tokyo (JP); Mizuki Takei, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 386 days.

(21) Appl. No.: 18/068,501

(22) Filed: Dec. 19, 2022

(65) Prior Publication Data

US 2023/0121783 A1    Apr. 20, 2023

Related U.S. Application Data

(63) Continuation of application No. PCT/JP2021/018612, filed on May 17, 2021.

(30) Foreign Application Priority Data

Jul. 21, 2020    (JP) .................................. 2020-124463

(51) Int. Cl.
*G06T 7/00* (2017.01)
*A61B 6/03* (2006.01)
(Continued)

(52) U.S. Cl.
CPC ............ *G06T 7/0012* (2013.01); *A61B 6/032* (2013.01); *A61B 6/463* (2013.01); *A61B 6/505* (2013.01);
(Continued)

(58) Field of Classification Search
CPC ............... G06T 7/0012; G06T 2200/04; G06T 2207/10081; G06T 2207/10088;
(Continued)

(56) References Cited

U.S. PATENT DOCUMENTS

2006/0271210 A1    11/2006    Subbu et al.
2007/0177782 A1*    8/2007    Raffy ...................... G06T 19/00
                                                              382/128

(Continued)

FOREIGN PATENT DOCUMENTS

JP    2006340835    12/2006
JP    2009183566    8/2009

(Continued)

OTHER PUBLICATIONS

"Office Action of Japan Counterpart Application", issued on Oct. 8, 2024, with English translation thereof, pp. 1-5.

(Continued)

*Primary Examiner* — Siamak Harandi
(74) *Attorney, Agent, or Firm* — JCIPRNET

(57) ABSTRACT

A medical image processing apparatus includes at least one processor, and the processor acquires a purpose of examination of a target medical image to be interpreted. The processor detects a first abnormal shadow from the target medical image and displays a detection result of the first abnormal shadow on a display. The processor sets, according to the purpose of the examination, a first detection threshold value for detecting the first abnormal shadow or a first display threshold value for displaying the detection result of the first abnormal shadow.

10 Claims, 7 Drawing Sheets

(51) Int. Cl.
*A61B 6/46* (2024.01)
*A61B 6/50* (2024.01)

(52) U.S. Cl.
CPC .............. *G06T 2200/04* (2013.01); *G06T 2207/10081* (2013.01); *G06T 2207/10088* (2013.01); *G06T 2207/20081* (2013.01); *G06T 2207/20084* (2013.01); *G06T 2207/30008* (2013.01); *G06T 2207/30061* (2013.01); *G06T 2207/30168* (2013.01)

(58) Field of Classification Search
CPC . G06T 2207/20081; G06T 2207/20084; G06T 2207/30008; G06T 2207/30061; G06T 2207/30168; A61B 6/032; A61B 6/463; A61B 6/505; A61B 6/469; A61B 6/545; A61B 6/502; A61B 6/03; A61B 6/5217
See application file for complete search history.

(56) References Cited

U.S. PATENT DOCUMENTS

2009/0097730 A1   4/2009  Kasai et al.
2019/0318828 A1*  10/2019 Li ..................... G16H 30/20
2020/0111558 A1*  4/2020  Matsumoto .......... G16H 50/20
2023/0121783 A1   4/2023  Nakamura et al.

FOREIGN PATENT DOCUMENTS

JP   2019188031   10/2019
JP   7361930      10/2023

OTHER PUBLICATIONS

"Notice of Reasons for Refusal of Japan Related Application No. 2023-171906", issued on Jul. 30, 2024, with English translation thereof, p. 1-p. 5.

Office Action of Japan Counterpart Application, with English translation thereof, issued on Jul. 11, 2023, pp. 1-5.

"International Search Report (Form PCT/ISA/210) of PCT/JP2021/018612," mailed on Jul. 20, 2021, with English translation thereof, pp. 1-5.

"Written Opinion of the International Searching Authority (Form PCT/ISA/237) of PCT/ JP2021/018612," mailed on Jul. 20, 2021, with English translation thereof, pp. 1-8.

* cited by examiner

MEDICAL IMAGE PROCESSING APPARATUS, METHOD, AND PROGRAM FOR DETECTING ABNORMAL REGION BY SETTING THRESHOLD

CROSS REFERENCE TO RELATED APPLICATIONS

The present application is a Continuation of PCT International Application No. PCT/JP2021/018612, filed on May 17, 2021, which claims priority to Japanese Patent Application No. 2020-124463, filed on Jul. 21, 2020. Each application above is hereby expressly incorporated by reference, in its entirety, into the present application.

BACKGROUND

Technical Field

The present disclosure relates to a medical image processing apparatus, method, and program.

Related Art

In recent years, advances in medical devices, such as computed tomography (CT) apparatuses and magnetic resonance imaging (MRI) apparatuses, have enabled image diagnosis using high-resolution medical images with higher quality. In particular, since a region of a lesion can be accurately specified by image diagnosis using CT images, MRI images, and the like, appropriate treatment is being performed based on the specified result.

In addition, image diagnosis is also made by analyzing a medical image via computer-aided diagnosis (CAD) using a learning model in which machine learning is performed by deep learning or the like, discriminating properties such as the shape, density, position, and size of structures of interest such as abnormal shadow candidates included in the medical images, and acquiring them as an analysis result. Furthermore, studies on region extraction of lesions and the like and discrimination between benign and malignant lesions using a learning model have also been conducted.

Incidentally, for an emergency patient such as a traffic accident, it is necessary to quickly and accurately diagnose a fracture such as a rib. For example, in a case where a rib is severely fractured, it is highly likely that the broken rib has damaged the internal organs, and quick treatment is required. On the other hand, even though the fracture is only a crack, the patient feels pain, so that appropriate treatment is required even though surgery is not necessary. Here, since ribs are curved, in a case of diagnosing a fracture using a three-dimensional image such as a CT image, one rib is present across a plurality of tomographic images. For this reason, it is necessary to observe tomographic images many times in order to diagnose a rib fracture and specify a fractured portion. As a result, it takes time for the diagnosis to specify the fracture, and the burden on a radiologist is large. Furthermore, a fracture of the degree of cracks may be overlooked because changes in the bone are unlikely to appear in the image because the displacement or rupture of the bone cortex is very slight.

Therefore, for example, a method of adjusting the number of displayed abnormal shadows by setting a threshold value for detecting abnormal shadows for each radiologist has been proposed (see, for example, JP2006-340835A).

Incidentally, in performing the interpretation of a medical image, a region to which a radiologist pays attention to the interpretation differs depending on a purpose of examination. For example, in a case where the purpose is to examine a fracture, the patient feels pain even though the fracture is only a crack as described above. For this reason, it is also necessary to specify all slight changes in properties that seem to be suspicious of whether or not the fracture occurs at first glance (the findings such as the presence or absence of clinical findings such as pain, such as irregularity or bending of the bone cortex, or the findings that the determination of whether or not the fracture occurs depends on the doctor's criteria), without overlooking them. On the other hand, in a case where the purpose is to examine diseases other than a fracture, it is necessary to find the fracture, but in a case where even a slight change in properties as described above is detected, it becomes difficult to pay attention to the diseases other than the fracture. Therefore, diseases other than the fracture may be overlooked. As a result, since it is necessary for the radiologist to interpret all the detection results of the fracture shadow, the interpretation cannot be performed efficiently.

SUMMARY OF THE INVENTION

The present disclosure has been made in consideration of the above circumstances, and an object thereof is to enable efficient interpretation.

According to an aspect of the present disclosure, there is provided a medical image processing apparatus comprising at least one processor, in which the processor is configured to acquire a purpose of examination of a target medical image to be interpreted, detect a first abnormal shadow from the target medical image, display a detection result of the first abnormal shadow on a display, and set, according to the purpose of the examination, a first detection threshold value for detecting the first abnormal shadow or a first display threshold value for displaying the detection result of the first abnormal shadow.

In the medical image processing apparatus according to the aspect of the present disclosure, the processor may be configured to acquire the purpose of the examination based on an operation history by an operator.

In addition, in the medical image processing apparatus according to the aspect of the present disclosure, the operation history may be a gradation condition set for interpretation of the target medical image.

In addition, in the medical image processing apparatus according to the aspect of the present disclosure, the operation history may be a display time of a part including the first abnormal shadow in the target medical image during interpretation before the detection of the first abnormal shadow from the target medical image.

In addition, in the medical image processing apparatus according to the aspect of the present disclosure, the first abnormal shadow may be an abnormal shadow of a fracture.

In this case, a part of the fracture may be a rib.

In addition, in the medical image processing apparatus according to the aspect of the present disclosure, the processor may be configured to detect at least one second abnormal shadow from the target medical image at a part different from a part including the first abnormal shadow, display a detection result of the second abnormal shadow on the display, and set, according to the purpose of the examination, a second detection threshold value for detecting the second abnormal shadow or a second display threshold value for displaying the detection result of the second abnormal shadow.

In addition, in the medical image processing apparatus according to the aspect of the present disclosure, the target medical image may be a three-dimensional image consisting of a plurality of tomographic images.

According to another aspect of the present disclosure, there is provided a medical image processing method comprising acquiring a purpose of examination of a target medical image to be interpreted, detecting a first abnormal shadow from the target medical image, displaying a detection result of the first abnormal shadow on a display, and setting, according to the purpose of the examination, a first detection threshold value for detecting the first abnormal shadow or a first display threshold value for displaying the detection result of the first abnormal shadow.

In addition, a program for causing a computer to execute the medical image processing method according to the aspect of the present disclosure may be provided.

According to the aspects of the present disclosure, the interpretation can be efficiently performed.

DETAILED DESCRIPTION

Figure 1:
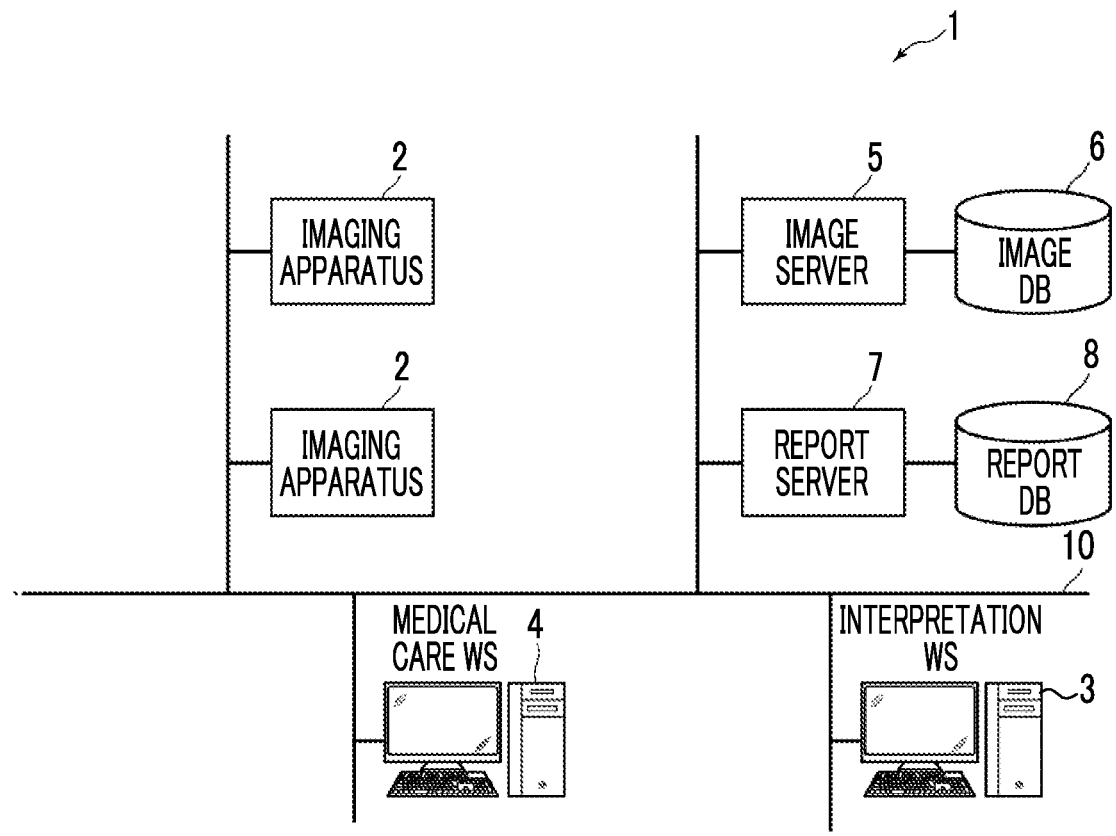
FIG. 1 is a diagram showing a schematic configuration of a medical information system to which a medical image processing apparatus according to a first embodiment of the present disclosure is applied.

Hereinafter, an embodiment of the present disclosure will be described with reference to the drawings. First, a configuration of a medical information system 1 to which a medical image processing apparatus according to the present embodiment is applied will be described. FIG. 1 is a diagram showing a schematic configuration of the medical information system 1. The medical information system 1 shown in FIG. 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

As shown in FIG. 1, in the medical information system 1, a plurality of imaging apparatuses 2, a plurality of interpretation workstations (WSs) 3 that are interpretation terminals, a medical care WS 4, an image server 5, an image database (hereinafter referred to as an image DB) 6, a report server 7, and a report database (hereinafter referred to as a report DB) 8 are communicably connected to each other through a wired or wireless network 10.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed on the computer from the recording medium. Alternatively, the application program is stored in a storage apparatus of a server computer connected to the network 10 or in a network storage in a state in which it can be accessed from the outside, and is downloaded to and installed on the computer in response to a request.

The imaging apparatus 2 is an apparatus (modality) that generates a medical image showing a diagnosis target part of the subject by imaging the diagnosis target part. Specifically, examples of the modality include a simple X-ray imaging apparatus, a CT apparatus, an MRI apparatus, a positron emission tomography (PET) apparatus, and the like. The medical image generated by the imaging apparatus 2 is transmitted to the image server 5 and is saved in the image DB 6.

The interpretation WS 3 is a computer used by, for example, a radiologist of a radiology department to interpret a medical image and to create an interpretation report, and encompasses a medical image processing apparatus 20 according to a first embodiment. In the interpretation WS 3, a viewing request for a medical image to the image server 5, various image processing for the medical image received from the image server 5, display of the medical image, input reception of comments on findings regarding the medical image, and the like are performed. In the interpretation WS 3, creation of an interpretation report, a registration request and a viewing request for the interpretation report to the report server 7, display of the interpretation report received from the report server 7, and the like are performed. The above processes are performed by the interpretation WS 3 executing software programs for respective processes.

The medical care WS 4 is a computer used by a doctor in a medical department to observe an image in detail, view an interpretation report, create an electronic medical record, and the like, and is configured to include a processing apparatus, a display apparatus such as a display, and an input apparatus such as a keyboard and a mouse. In the medical care WS 4, a viewing request for the image to the image server 5, display of the image received from the image server 5, a viewing request for the interpretation report to the report server 7, and display of the interpretation report received from the report server 7 are performed. The above processes are performed by the medical care WS 4 executing software programs for respective processes.

The image server 5 is a general-purpose computer on which a software program that provides a function of a database management system (DBMS) is installed. The image server 5 comprises a storage in which the image DB 6 is configured. This storage may be a hard disk apparatus connected to the image server 5 by a data bus, or may be a disk apparatus connected to a storage area network (SAN) or a network attached storage (NAS) connected to the network 10. In a case where the image server 5 receives a request to register a medical image from the imaging apparatus 2, the image server 5 prepares the medical image in a format for a database and registers the medical image in the image DB 6.

Image data of the medical image acquired by the imaging apparatus 2 and accessory information are registered in the image DB 6. The accessory information includes, for example, an image identification (ID) for identifying each medical image, a patient ID for identifying a subject, an examination ID for identifying an examination, a unique ID (unique identification (UID)) allocated for each medical image, examination date and examination time at which a medical image is generated, the type of imaging apparatus used in an examination for acquiring a medical image, patient information such as the name, age, and gender of a patient, an examination part (an imaging part), imaging information (an imaging protocol, an imaging sequence, an imaging method, imaging conditions, the use of a contrast medium, and the like), and information such as a series number or a collection number in a case where a plurality of medical images are acquired in one examination.

In addition, in a case where the viewing request from the interpretation WS 3 and the medical care WS 4 is received through the network 10, the image server 5 searches for a medical image registered in the image DB 6 and transmits the searched for medical image to the interpretation WS 3 and to the medical care WS 4 that are request sources.

The report server 7 incorporates a software program for providing a function of a database management system to a general-purpose computer. In a case where the report server 7 receives a request to register the interpretation report from the interpretation WS 3, the report server 7 prepares the interpretation report in a format for a database and registers the interpretation report in the report DB 8.

In the report DB 8, an interpretation report created by the radiologist using the interpretation WS 3 is registered. The interpretation report may include information such as, for example, a medical image to be interpreted, an image ID for identifying the medical image, a radiologist ID for identifying the radiologist who performed the interpretation, a disease name, disease position information, and information for accessing a medical image.

Further, in a case where the report server 7 receives the viewing request for the interpretation report from the interpretation WS 3 and the medical care WS 4 through the network 10, the report server 7 searches for the interpretation report registered in the report DB 8, and transmits the searched for interpretation report to the interpretation WS 3 and to the medical care WS 4 that are request sources.

In the present embodiment, it is assumed that the medical image is a three-dimensional CT image consisting of a plurality of tomographic images with a chest as a diagnosis target, and an interpretation report including comments on findings for a rib fracture or a lung disease included in the chest is created by interpreting the CT image. The medical image is not limited to the CT image, and any medical image such as an MRI image and a simple two-dimensional image acquired by a simple X-ray imaging apparatus can be used.

In the present embodiment, in creating the interpretation report, the radiologist first displays a medical image on a display 14 and interprets the medical image with his/her own eyes. After that, the medical image processing apparatus according to the present embodiment detects a fracture part or a lung disease as an abnormal shadow from the medical image, and performs a second interpretation using the detection result. The first interpretation is referred to as a primary interpretation, and the second interpretation using the detection result of the abnormal shadow by the medical image processing apparatus according to the present embodiment is referred to as a secondary interpretation.

The network 10 is a wired or wireless local area network that connects various apparatuses in a hospital to each other. In a case where the interpretation WS 3 is installed in another hospital or clinic, the network 10 may be configured to connect local area networks of respective hospitals through the Internet or a dedicated line.

Figure 2:
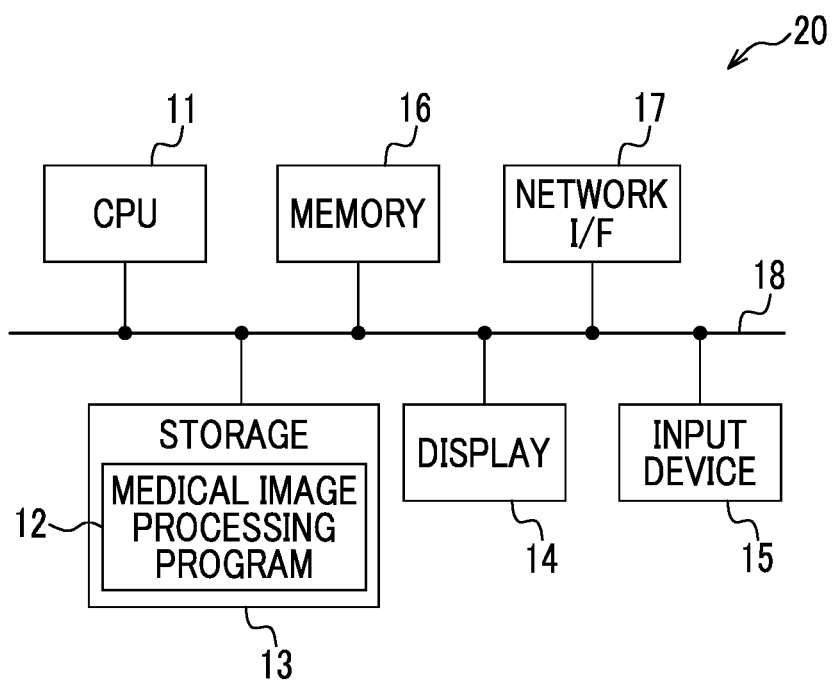
FIG. 2 is a diagram showing a schematic configuration of the medical image processing apparatus according to the first embodiment.

Next, the medical image processing apparatus according to the first embodiment will be described. FIG. 2 describes a hardware configuration of the medical image processing apparatus according to the first embodiment. As shown in FIG. 2, the medical image processing apparatus 20 includes a central processing unit (CPU) 11, a non-volatile storage 13, and a memory 16 as a temporary storage area. Further, the medical image processing apparatus 20 includes a display 14 such as a liquid crystal display, an input device 15 such as a keyboard and a mouse, and a network interface (I/F) 17 connected to the network 10. The CPU 11, the storage 13, the display 14, the input device 15, the memory 16, and the network I/F 17 are connected to a bus 18. The CPU 11 is an example of a processor in the present disclosure.

The storage 13 is realized by a hard disk drive (HDD), a solid state drive (SSD), a flash memory, and the like. A medical image processing program 12 is stored in the storage 13 as the storage medium. The CPU 11 reads the medical image processing program 12 from the storage 13, loads the read program into the memory 16, and executes the loaded medical image processing program 12.

Figure 3:
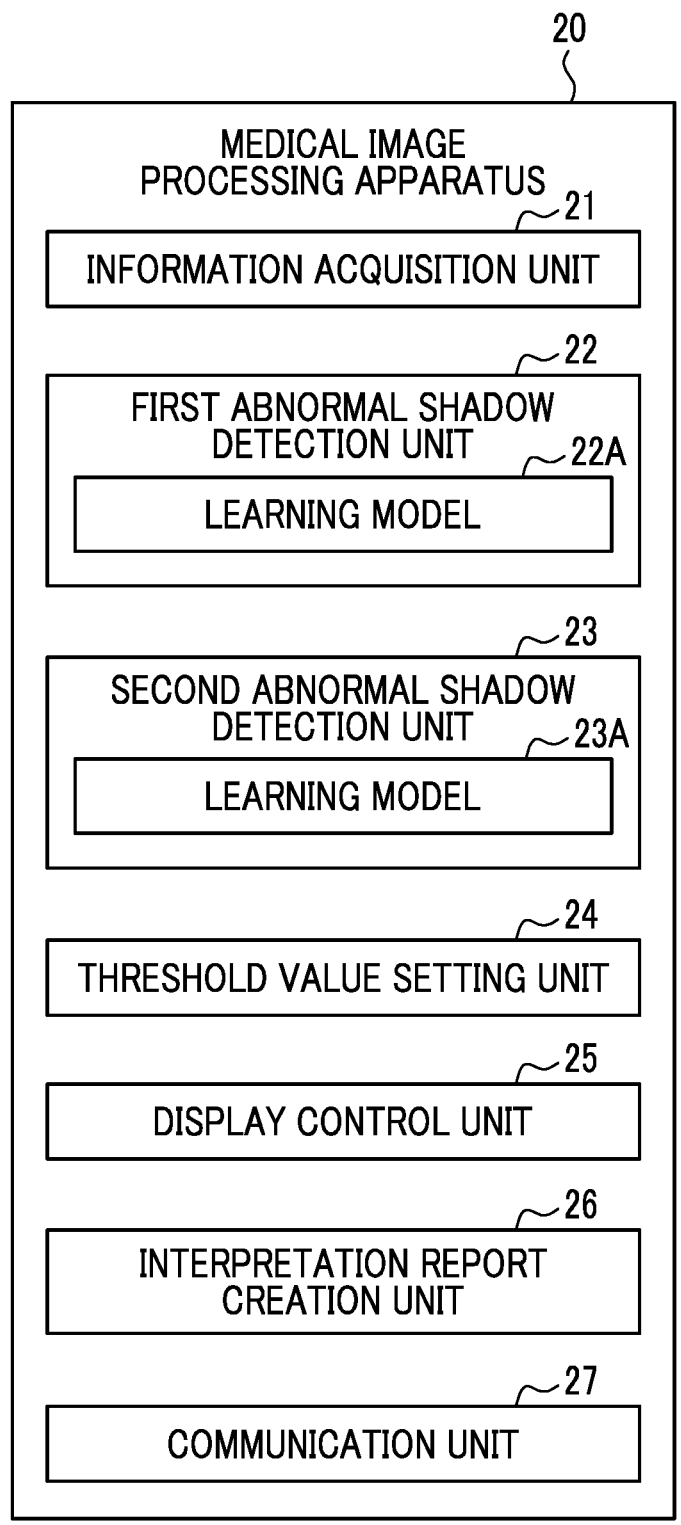
FIG. 3 is a functional configuration diagram of the medical image processing apparatus according to the first embodiment.

Next, a functional configuration of the medical image processing apparatus according to the first embodiment will be described. FIG. 3 is a diagram showing a functional configuration of the medical image processing apparatus according to the first embodiment. As shown in FIG. 3, the medical image processing apparatus 20 comprises an information acquisition unit 21, a first abnormal shadow detection unit 22, a second abnormal shadow detection unit 23, a threshold value setting unit 24, a display control unit 25, an interpretation report creation unit 26, and a communication unit 27. Then, as the CPU 11 executes the medical image processing program 12, the CPU 11 functions as the information acquisition unit 21, the first abnormal shadow detection unit 22, the second abnormal shadow detection unit 23, the threshold value setting unit 24, the display control unit 25, the interpretation report creation unit 26, and the communication unit 27.

The information acquisition unit 21 acquires a target medical image G0 to be processed for creating an interpretation report from the image server 5 according to an instruction from the input device 15 by the radiologist who is an operator. As described above, the target medical image G0 is a three-dimensional CT image consisting of a plurality of tomographic images. In addition, in the first embodiment, it is assumed that the target medical image G0 is acquired by imaging the chest of the human body. In addition, the information acquisition unit 21 acquires a purpose of examination of the target medical image G0. In the first embodiment, the purpose of the examination includes, for example, checking of a fracture shadow and checking of abnormal shadows of diseases such as a lung other than the fracture. In addition, in the present embodiment, as checking of the abnormal shadow other than the fracture, it is assumed that the abnormal shadow of the lung disease (hereinafter referred to as the abnormal shadow of the lung) is checked.

In the first embodiment, the information acquisition unit 21 acquires the purpose of the examination by receiving the input of the purpose of the examination by the radiologist using the input device 15. On the other hand, the information acquisition unit 21 may acquire the purpose of the examination based on the operation history of the radiologist. For example, in a case where the radiologist sets a gradation condition suitable for interpretation of a fracture, that is, a bone condition in displaying the target medical image G0, the information acquisition unit 21 acquires checking of the fracture shadow as the purpose of the examination. In addition, in a case where the radiologist sets a gradation condition suitable for interpretation of an abnormal shadow of a disease other than the fracture, for example, an abnormal shadow of the lung, the information acquisition unit 21 acquires checking of the abnormal shadow of the lung as the purpose of the examination. The gradation condition may be a case in which the primary interpretation is performed or a case in which the secondary interpretation is performed.

Here, the gradation condition is a window value and a window width in displaying the target medical image G0 on the display 14. The window value is a CT value that is the center of a part to be observed in the gradation that can be displayed by the display 14. The window width is a width between a lower limit value and an upper limit value of the CT value of the part to be observed. For example, in a case where the bone condition is set, the window value is the CT value of the bone, and the window width is the lower limit value and the upper limit value of the CT value such that the bone is easily seen. In a case where the bone condition is set as the gradation condition, the target medical image G0 in which the bone can be easily interpreted can be displayed on the display 14. On the other hand, in a case where the gradation condition suitable for the interpretation of the lung is set, the target medical image G0 in which the abnormal shadow of the lung can be easily interpreted can be displayed on the display 14.

In addition, the information acquisition unit 21 may acquire the purpose of the examination as the operation history based on the display time of a part including the abnormal shadow in the target medical image G0 in a case where the radiologist performs the primary interpretation. For example, in performing the primary interpretation, in a case where the display time of the tomographic image including the bone in the target medical image G0 is equal to or longer than a predetermined threshold value, the information acquisition unit 21 acquires the checking of the presence or absence of a fracture as the purpose of the examination. In the present embodiment, since the target medical image G0 includes the chest of the human body, it may be difficult to discriminate whether the purpose of the examination is to check the presence or absence of a fracture or to check an abnormal shadow of the lung, depending on the display time of the tomographic image in the case of the primary interpretation. However, in a case where the target medical image G0 includes not only the chest but also the abdomen, and in a case where the display time of the tomographic image including the bone is longer than the display time of the tomographic image of the abdomen, it is possible to acquire checking of the presence or absence of the fracture as the purpose of the examination. On the contrary, in a case where the display time of the tomographic image of the abdomen is longer, it is possible to acquire checking of the abnormal shadow of the abdomen as the purpose of the examination.

The first abnormal shadow detection unit 22 detects the shadow of the fracture in the rib included in the target medical image G0 as the abnormal shadow for the secondary interpretation. The first abnormal shadow detection unit 22 detects the shadow of the fracture as a first abnormal shadow from the target medical image G0 by using a known computer-aided diagnostic imaging (that is, CAD) algorithm. To this end, the first abnormal shadow detection unit 22 has a learning model 22A that has been machine-learned to detect a fracture shadow from the target medical image G0. In the first embodiment, the learning model 22A consists of a convolutional neural network (CNN) in which deep learning has been performed using supervised training data so as to discriminate whether or not each pixel (voxel) in the target medical image G0 represents a fracture shadow.

The learning model 22A is constructed by training CNN using a large amount of supervised training data consisting of supervised training images that include fracture shadows and correct answer data representing the position of the fracture shadows in the supervised training images, and a large amount of supervised training data consisting of supervised training images that do not include fracture shadows. The learning model 22A derives the probability (likelihood) indicating that each pixel in the medical image is a fracture, and detects pixels whose probability is equal to or higher than a predetermined first detection threshold value as pixels of the fracture shadows. Here, the probability is a value of 0 or more and 1 or less. The learning model 22A may detect a fracture shadow from a three-dimensional medical image, or may detect a fracture shadow from each of a plurality of tomographic images constituting the target medical image G0.

As the learning model 22A, any learning model such as, for example, a support vector machine (SVM) can be used in addition to the convolutional neural network.

The second abnormal shadow detection unit 23 detects the second abnormal shadow in the target medical image G0 for the secondary interpretation. In the first embodiment, the second abnormal shadow is defined as an abnormal shadow of the lung. To this end, the second abnormal shadow detection unit 23 detects the abnormal shadow of the lung as the second abnormal shadow from the target medical image G0 using the CAD algorithm, similarly to the first abnormal shadow detection unit 22. To this end, the second abnormal shadow detection unit 23 has a learning model 23A that has been machine-learned to detect an abnormal shadow of the lung from the target medical image G0. In the first embodiment, the learning model 23A consists of a convolutional neural network (CNN) in which deep learning has been performed using supervised training data so as to discriminate whether or not each pixel (voxel) in the target medical image G0 represents an abnormal shadow of the lung.

The learning model 23A is constructed by training CNN using a large amount of supervised training data consisting of supervised training images that include abnormal shadows of the lung and correct answer data representing the position of the abnormal shadows of the lung in the supervised training images, and a large amount of supervised training data consisting of supervised training images that do not include abnormal shadows of the lung. The learning model 23A derives the probability (likelihood) indicating that each pixel in the medical image is abnormal shadows of the lung, and detects pixels whose probability is equal to or higher than a predetermined second detection threshold value as pixels of the abnormal shadows of the lung. Here, the probability is a value of 0 or more and 1 or less. The learning model 23A may detect an abnormal shadow of the lung from a three-dimensional medical image, or may detect an abnormal shadow of the lung from each of a plurality of tomographic images constituting the target medical image G0.

Further, as the learning model 23A, for example, any learning model such as a support vector machine can be used, in addition to the convolutional neural network.

In the secondary interpretation, the threshold value setting unit 24 sets, according to the purpose of the examination, a first detection threshold value in a case where the first abnormal shadow detection unit 22 detects a fracture shadow and a second detection threshold value in a case where the second abnormal shadow detection unit 23 detects an abnormal shadow of the lung. Here, in the first embodiment, two values, Th11 and Th12, are prepared and stored in the storage 13 as the first detection threshold value. Th11<Th12, for example, Th11=0.30 and Th12=0.80. In addition, two values, Th21 and Th22, are prepared and stored in the storage 13 as the second detection threshold value. Th21<Th22, for example, Th21=0.30 and Th22=0.80.

In a case where the purpose of the examination is to check the fracture shadow, the threshold value setting unit 24 sets the first detection threshold value to the smaller value Th11. In addition, the threshold value setting unit 24 sets the second detection threshold value to the larger value Th22. Accordingly, the first abnormal shadow detection unit 22 detects the abnormal shadow of the bone including not only the fracture shadow of the complete fracture but also the shadow exhibiting a slight change in properties suspected to be a fracture. In addition, the second abnormal shadow detection unit 23 does not detect the shadow of the lung exhibiting a slight change in properties suspected to be abnormal.

In addition, in a case where the purpose of the examination is to check an abnormal shadow of the lung other than a fracture shadow, the threshold value setting unit 24 sets the first detection threshold value to the larger value Th12. Further, the threshold value setting unit 24 sets the second detection threshold value to the smaller value Th21. Accordingly, the first abnormal shadow detection unit 22 does not detect the shadow of the bone exhibiting a slight change in properties suspected to be a fracture. In addition, the second abnormal shadow detection unit 23 detects the abnormal shadow of the lung, including the shadow of the lung exhibiting a slight change in properties suspected to be abnormal.

Figure 4:
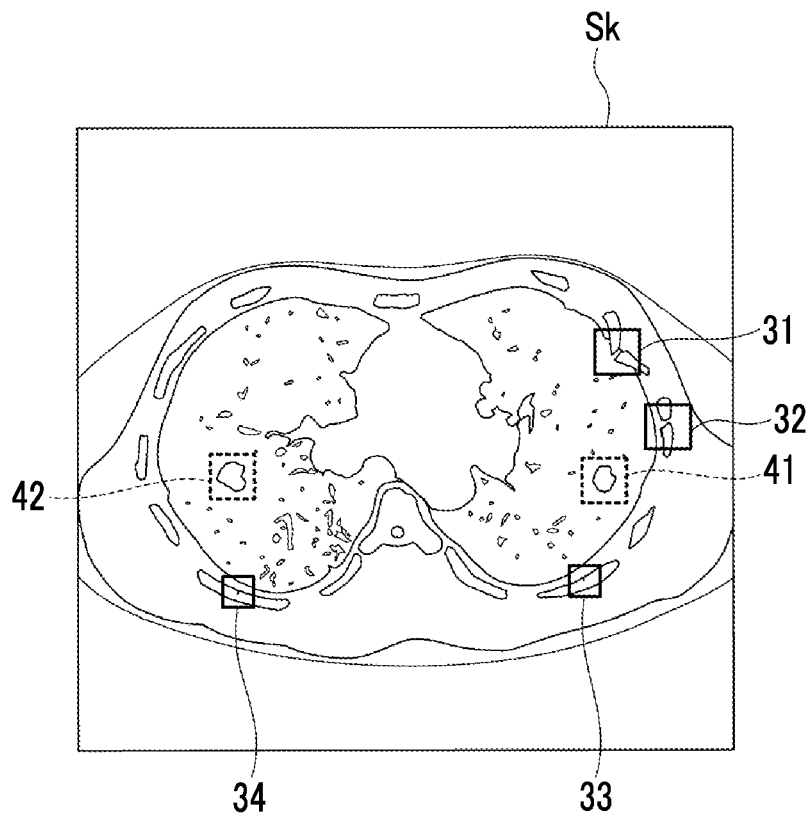
FIG. 4 is a diagram showing a detection result in a case where a purpose of examination is to check fracture shadows.

FIG. 4 is a diagram showing a detection result in a case where a purpose of examination is to check the presence or absence of a fracture. Note that FIG. 4 shows a state in which the detection result is superimposed and displayed on one tomographic image Sk in the target medical image G0. As shown in FIG. 4, in the tomographic image Sk, four fracture shadows 31 to 34 indicated by a solid line rectangle are detected, and two abnormal shadows 41 and 42 of the lung indicated by a broken line rectangle are detected. The fracture shadows 31 to 34 include shadows 33 and 34 suspected to be a fracture.

Figure 5:
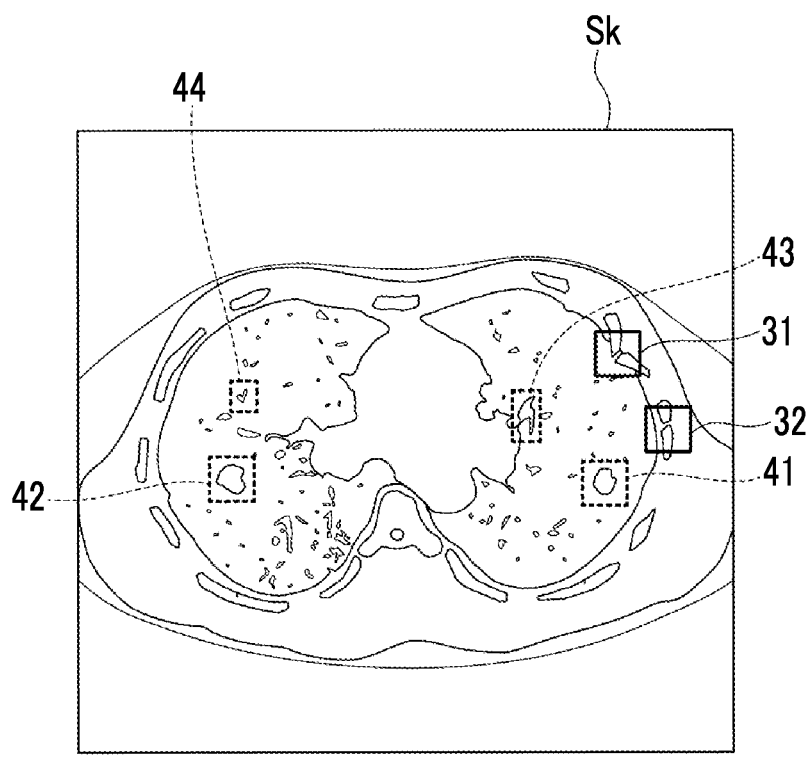
FIG. 5 is a diagram showing a detection result in a case where a purpose of examination is to check abnormal shadows other than fractures.

FIG. 5 is a diagram showing a detection result in a case where the purpose of the examination is to check an abnormal shadow of the lung. Note that FIG. 5 shows a state in which the detection result is superimposed and displayed on the same tomographic image Sk as in FIG. 4. As shown in FIG. 5, in the tomographic image Sk, two fracture shadows 31 and 32 indicated by a solid line rectangle are detected, and four abnormal shadows 41 to 44 of the lung indicated by a broken line rectangle are detected.

Comparing FIG. 4 and FIG. 5, in FIG. 4, all the fracture shadows 31 to 34 including the shadow of the bone exhibiting a slight change in properties suspected to be fractures are detected. On the other hand, in FIG. 5, the shadows 33 and 34 of the bones exhibiting a slight change in properties suspected to be fractures are not detected, and only the fracture shadows 31 and 32 that can be regarded as positive are detected. Further, in FIG. 4, only the abnormal shadows 41 and 42 of the lung that can be regarded as positive are detected, but in FIG. 5, all the abnormal shadows 41 to 44 of the lung including the shadow of the lung exhibiting a slight change in properties suspected to be abnormal are detected.

Figure 6:
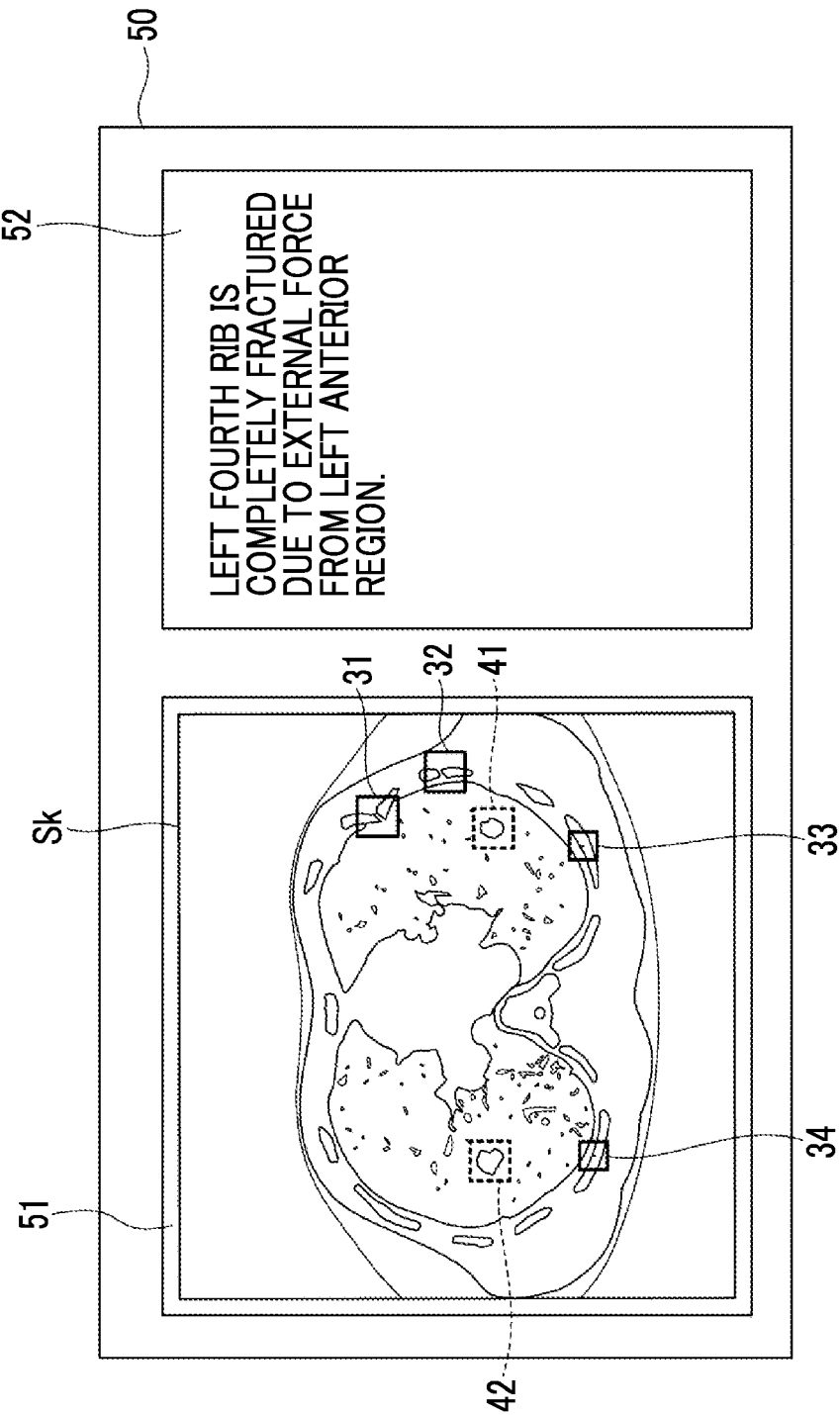
FIG. 6 is a diagram showing a display screen of an examination result.

The display control unit 25 displays the detection results of the fracture shadow and the abnormal shadow of the lung on the display 14. FIG. 6 is a diagram showing a display screen of a detection result. As shown in FIG. 6, a display screen 50 includes an image display region 51 and a report creation region 52. In the image display region 51, a plurality of tomographic images included in the target medical image G0 are displayed in a switchable manner. In FIG. 6, the tomographic image Sk including the detection result shown in FIG. 4 is displayed.

The radiologist inputs, to the report creation region 52, a comment on findings regarding the fracture shadow included in the target medical image G0 while switching and displaying the tomographic image included in the target medical image G0 using the input device 15.

The interpretation report creation unit 26 creates an interpretation report. For example, in FIG. 6, the comment on findings "The left fourth rib is completely fractured due to an external force from the left anterior region" is input to the report creation region 52. The interpretation report creation unit 26 creates an interpretation report including the input comment on findings. Then, the interpretation report creation unit 26 saves the created interpretation report together with the target medical image G0 and the detection result in the storage 13.

The communication unit 27 transfers the created interpretation report together with the target medical image G0 and the detection result to the report server 7. In the report server 7, the transferred interpretation report is saved together with the target medical image G0 and the detection result.

Figure 7:
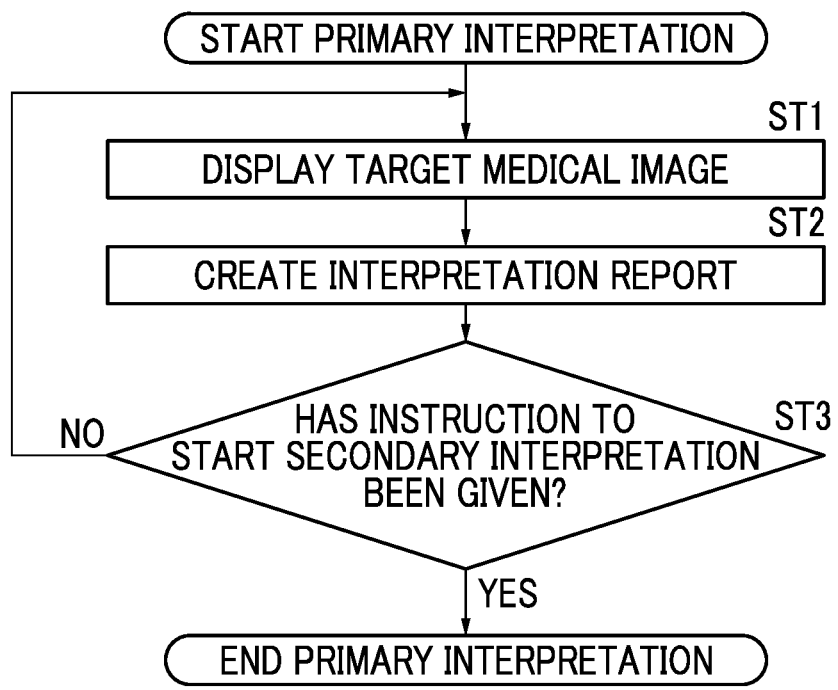
FIG. 7 is a flowchart showing a process performed during primary interpretation in the first embodiment.
Figure 8:
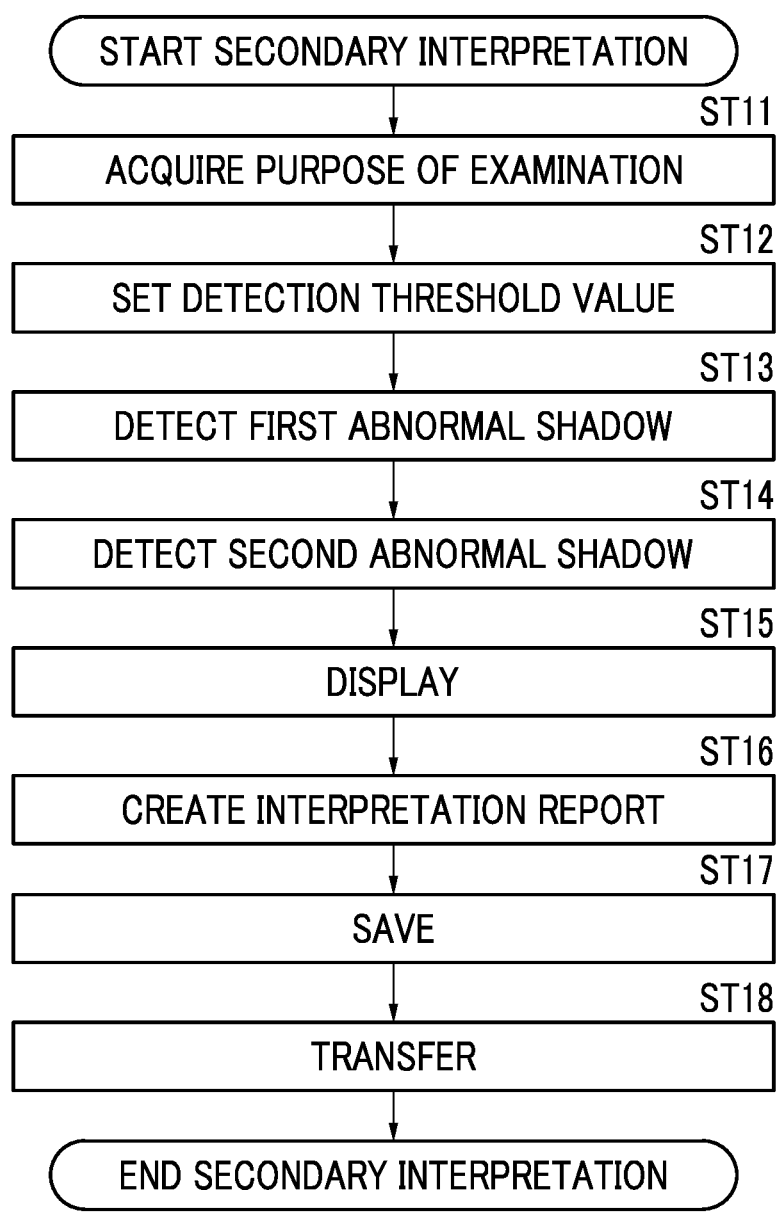
FIG. 8 is a flowchart showing a process performed during secondary interpretation in the first embodiment.

Next, a process performed in the first embodiment will be described. FIG. 7 is a flowchart showing a process performed during the primary interpretation in the first embodiment, and FIG. 8 is a flowchart showing a process performed during the secondary interpretation in the first embodiment. It is assumed that the target medical image G0 to be interpreted is acquired from the image server 5 by the information acquisition unit 21 and is saved in the storage 13. The process is started in a case where the radiologist issues an instruction to create an interpretation report, and the display control unit 25 displays the target medical image G0 on the display 14 (Step ST1). Next, the interpretation report creation unit 26 creates an interpretation report based on the primary interpretation using the comments on findings input by the radiologist (Step ST2). Next, it is determined whether or not the instruction to start the secondary interpretation has been given (Step ST3), and in a case where Step ST3 is negative, the process returns to Step ST1. In a case where Step ST3 is affirmative, the primary interpretation is terminated and the secondary interpretation is started.

At the time of the secondary interpretation, first, the information acquisition unit 21 acquires the purpose of the examination of the target medical image G0 (Step ST11). Next, the threshold value setting unit 24 sets, according to the purpose of the examination, a first detection threshold value in a case where a fracture shadow is detected as a first abnormal shadow and a second detection threshold value in a case where an abnormal shadow of the lung is detected as a second abnormal shadow (detection threshold value setting; Step ST12).

Subsequently, the first abnormal shadow detection unit 22 detects the first abnormal shadow in the target medical image G0, that is, the fracture shadow, using the first detection threshold value (Step ST13). Next, the second abnormal shadow detection unit 23 detects the second abnormal shadow in the target medical image G0, that is, the abnormal shadow of the lung, using the second detection threshold value (Step ST14).

Then, the display control unit 25 displays the target medical image G0 and the detection result on the display 14 (Step ST15). Next, the interpretation report creation unit 26 creates an interpretation report using the comments on findings input by the radiologist (Step ST16). Then, the interpretation report creation unit 26 saves the created interpretation report together with the target medical image G0 and the detection result in the storage 13 (Step ST17). Further, the communication unit 27 transfers the created interpretation report together with the target medical image G0 and the detection result to the report server 7 (Step ST18), and ends the process of the secondary interpretation.

In this way, in the first embodiment, the first detection threshold value for detecting the fracture shadow, that is, the first abnormal shadow is set according to the purpose of the examination. Therefore, in a case where the purpose of the examination is to check the first abnormal shadow, the first detection threshold value can be decreased to detect the first abnormal shadow including a shadow exhibiting a slight change in properties suspected to be abnormal. Thereby, in the first embodiment, it is possible to prevent the first abnormal shadow from being overlooked. In addition, in a case where the purpose of the examination is to check the second abnormal shadow, the first detection threshold value can be increased so as not to detect, as the first abnormal shadow, a shadow exhibiting a slight change in properties suspected to be abnormal. Accordingly, it is possible to efficiently perform interpretation by paying attention to the second abnormal shadow without paying attention to the shadow exhibiting a slight change in properties suspected to be abnormal.

In addition, in the first embodiment, the second detection threshold value for detecting the abnormal shadow of the lung, that is, the second abnormal shadow is also set according to the purpose of the examination. Therefore, in a case where the purpose of the examination is to check the first abnormal shadow, the second detection threshold value can be increased so as not to detect, as the second abnormal shadow, a shadow exhibiting a slight change in properties suspected to be abnormal. Accordingly, in the first embodiment, it is possible to efficiently perform interpretation by paying attention to the first abnormal shadow without paying attention to the shadow exhibiting a slight change in properties suspected to be abnormal. In addition, in a case where the purpose of the examination is to check the second abnormal shadow, the second detection threshold value can be decreased to detect the second abnormal shadow including a shadow exhibiting a slight change in properties suspected to be abnormal. Thereby, it is possible to prevent the second abnormal shadow from being overlooked.

Next, a second embodiment of the present disclosure will be described. Since the configuration of a medical image processing apparatus according to the second embodiment is the same as the configuration of the medical image processing apparatus according to the first embodiment shown in FIGS. 2 and 3 and only the processing to be performed is different, detailed description of the apparatus will be omitted here. In the first embodiment, the threshold value setting unit 24 sets, according to the purpose of the examination, the first detection threshold value in the first abnormal shadow detection unit 22 and the second detection threshold value in the second abnormal shadow detection unit 23. The second embodiment is different from the first embodiment in that the threshold value setting unit 24 sets a threshold value in a case where the display control unit 25 displays the detection result on the display 14 as a display threshold value.

In the second embodiment, the first abnormal shadow detection unit 22 detects the first abnormal shadow, that is, the fracture shadow, using a predetermined first detection threshold value. In addition, the second abnormal shadow detection unit 23 detects the second abnormal shadow, that is, the abnormal shadow of the lung, using a predetermined second detection threshold value. In addition, as the predetermined first detection threshold value, the smaller threshold value Th11 in the first embodiment may be used. In addition, as the predetermined second detection threshold value, the smaller threshold value Th21 in the first embodiment may be used.

In the second embodiment, the threshold value setting unit 24 sets a first display threshold value and a second display threshold value on the display control unit 25 according to the purpose of the examination. Here, in the second embodiment, two values, Th31 and Th32, are prepared and stored in the storage 13 as the first display threshold value. Th31<Th32, and specific values thereof are, for example, Th31=0.30 and Th32=0.80. In addition, two values, Th41 and Th42, are prepared and stored in the storage 13 as the second display threshold value. Th41<Th42, and specific values thereof are, for example, Th41=0.30 and Th42=0.80.

In a case where the purpose of the examination is to check the presence or absence of a fracture, the threshold value setting unit 24 sets the first display threshold value to the smaller value Th31. In addition, the threshold value setting unit 24 sets the second display threshold value to the larger value Th42. Thereby, the display control unit 25 displays the shadows of all the bones detected by the first abnormal shadow detection unit 22 on the display 14. That is, the display control unit 25 displays not only the fracture shadow of a complete fracture but also the fracture shadow exhibiting a slight change in properties suspected to be a fracture on the display 14. In addition, the display control unit 25 does not display, on the display 14, the abnormal shadow of the lung exhibiting a slight change in properties suspected to be abnormal among all the shadows of the lung detected by the second abnormal shadow detection unit 23.

In addition, in a case where the purpose of the examination is to check an abnormal shadow of the lung other than the fracture, the threshold value setting unit 24 sets the first display threshold value to the larger value Th32. In addition, the threshold value setting unit 24 sets the second display threshold value to the smaller value Th41. Accordingly, the display control unit 25 does not display, on the display 14, the fracture shadow exhibiting a slight change in properties suspected to be a fracture among all the fracture shadows detected by the first abnormal shadow detection unit 22. In addition, the display control unit 25 displays the abnormal shadows of all the lungs detected by the second abnormal shadow detection unit 23 on the display 14. That is, the display control unit 25 displays the abnormal shadows of all the lungs including the abnormal shadows of the lungs exhibiting a slight change in properties suspected to be abnormal on the display 14.

In the second embodiment, in a case where the purpose of the examination is to check the presence or absence of a fracture, a detection result similar to the detection result shown in FIG. 4 is displayed on the display 14. In addition, in a case where the purpose of the examination is to check an abnormal shadow of the lung other than the fracture, a detection result similar to the detection result shown in FIG. 5 is displayed on the display 14.

Figure 9:
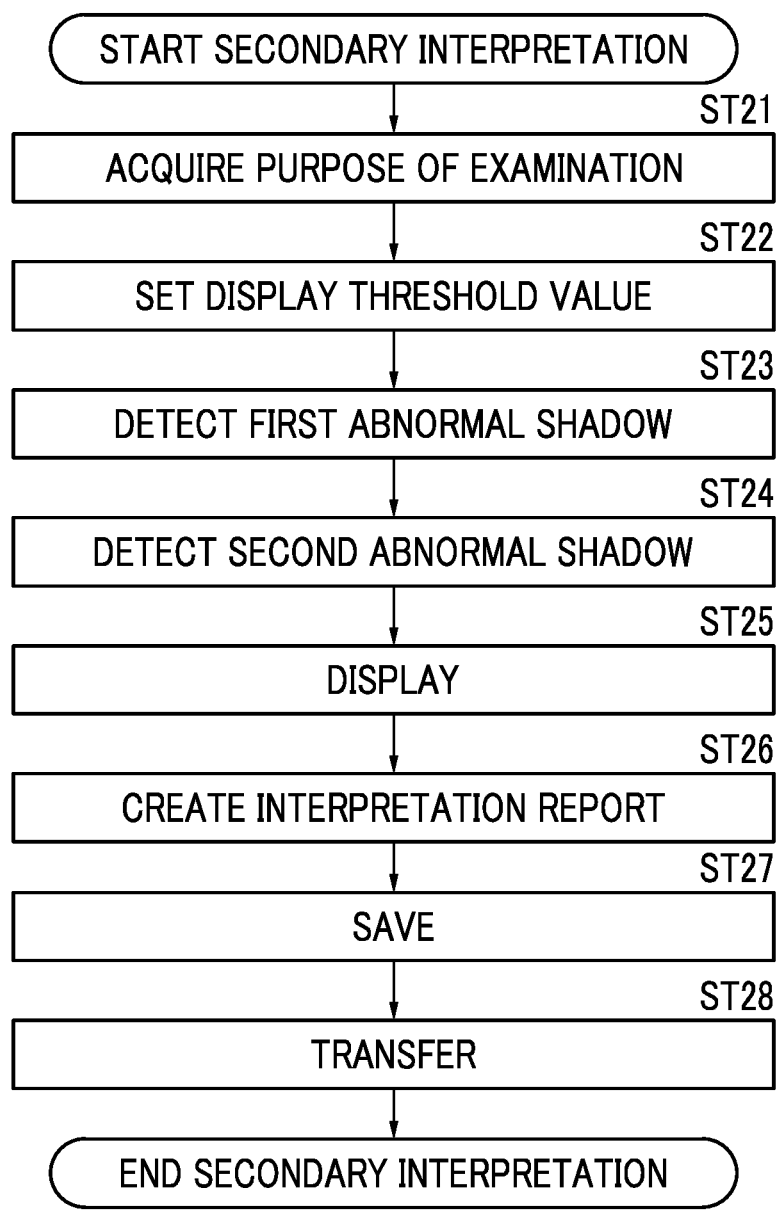
FIG. 9 is a flowchart showing a process performed during secondary interpretation in a second embodiment.

Next, a process performed in the second embodiment will be described. It is assumed that the target medical image G0 to be interpreted is acquired from the image server 5 by the information acquisition unit 21 and is saved in the storage 13. In addition, in the second embodiment, a process performed during the primary interpretation is the same as the process performed in the first embodiment shown in FIG. 7. Therefore, only a process performed during the secondary interpretation will be described here. FIG. 9 is a flowchart showing a process performed during secondary interpretation in the second embodiment.

At the time of the secondary interpretation, first, the information acquisition unit 21 acquires the purpose of the examination of the target medical image G0 (Step ST21). Next, the threshold value setting unit 24 sets, according to the purpose of the examination, a first display threshold value in a case where a fracture shadow is displayed as a first abnormal shadow and a second display threshold value in a case where an abnormal shadow of the lung is displayed as a second abnormal shadow (display threshold value setting; Step ST22).

Subsequently, the first abnormal shadow detection unit 22 detects the first abnormal shadow in the target medical image G0, that is, the fracture shadow (Step ST23). Next, the second abnormal shadow detection unit 23 detects the second abnormal shadow in the target medical image G0, that is, the abnormal shadow of the lung (Step ST24).

Then, the display control unit 25 displays the target medical image G0 and the detection result on the display 14 using the first display threshold value and the second display threshold value (Step ST25). Next, the interpretation report creation unit 26 creates an interpretation report using the comments on findings input by the radiologist (Step ST26). Then, the interpretation report creation unit 26 saves the created interpretation report together with the target medical image G0 and the detection result in the storage 13 (Step ST27). Further, the communication unit 27 transfers the created interpretation report together with the target medical image G0 and the detection result to the report server 7 (Step ST28), and ends the process. In the second embodiment, the detection result saved in the storage 13 or transferred to the report server 7 may be only the detection result displayed on the display 14, or may be all detection results detected by the first abnormal shadow detection unit 22 and the second abnormal shadow detection unit 23.

In this way, in the second embodiment, the first display threshold value for displaying the fracture shadow, that is, the first abnormal shadow is set according to the purpose of the examination. Therefore, in a case where the purpose of the examination is to check the first abnormal shadow, the first display threshold value can be decreased to display the first abnormal shadow including a shadow exhibiting a slight change in properties suspected to be abnormal. Thereby, also in the second embodiment, it is possible to prevent the first abnormal shadow from being overlooked. In addition, in a case where the purpose of the examination is to check the first abnormal shadow, the first display threshold value can be increased so as not to display, as the first abnormal shadow, a shadow exhibiting a slight change in properties suspected to be abnormal. Accordingly, it is possible to efficiently perform interpretation by paying attention to the second abnormal shadow without paying attention to the shadow exhibiting a slight change in properties suspected to be abnormal.

In addition, in the second embodiment, the second display threshold value for displaying the abnormal shadow of the lung, that is, the second abnormal shadow is also set according to the purpose of the examination. Therefore, in a case where the purpose of the examination is to check the first abnormal shadow, the second display threshold value can be increased so as not to display, as the second abnormal shadow, a shadow exhibiting a slight change in properties suspected to be abnormal. Accordingly, also in the second embodiment, it is possible to efficiently perform interpretation by paying attention to the first abnormal shadow without paying attention to the shadow exhibiting a slight change in properties suspected to be abnormal. In addition, in a case where the purpose of the examination is to check the second abnormal shadow, the second display threshold value can be decreased to display the second abnormal shadow including a shadow exhibiting a slight change in properties suspected to be abnormal. Thereby, it is possible to prevent the second abnormal shadow from being overlooked.

In the first embodiment, the threshold value setting unit 24 sets the first detection threshold value in the first abnormal shadow detection unit 22 and the second detection threshold value in the second abnormal shadow detection unit 23, but the present disclosure is not limited thereto. The threshold value setting unit 24 may set only the first detection threshold value in the first abnormal shadow detection unit 22 or only the second detection threshold value in the second abnormal shadow detection unit 23.

In addition, in the second embodiment, the threshold value setting unit 24 sets the first display threshold value for displaying the first abnormal shadow and the second display threshold value for displaying the second abnormal shadow, but the present disclosure is not limited thereto. The threshold value setting unit 24 may set only the first display threshold value for displaying the first abnormal shadow or only the second display threshold value for displaying the second abnormal shadow.

In addition, in each of the above-described embodiments, the medical image processing apparatus according to the present embodiment is applied in a case of performing the primary interpretation and the secondary interpretation, but the present disclosure is not limited thereto. It is also possible to apply the processing according to the present embodiment even in a case where only the secondary interpretation, that is, the abnormal shadow in the target medical image G0 is specified and only the interpretation using the result of the specified abnormal shadow is performed. In this case, the display time of the image including the target part at the time of the primary interpretation cannot be used as the operation history, but it is possible to acquire the purpose of the examination input by the radiologist or the purpose of the examination using or the set gradation condition.

In addition, in each of the above-described embodiments, the fracture shadow is used as the first abnormal shadow, but the first abnormal shadow is not limited thereto. In the case of an abnormal shadow of a disease in which the first abnormal shadow and the second abnormal shadow are different from each other, in addition to the fracture, the abnormal shadows of a disease of any part of the human body, such as the heart, the liver, the brain, and the limbs can be the first abnormal shadow. In this case, the learning model 22A of the first abnormal shadow detection unit 22 is trained using the supervised training data so that the abnormal shadow of the target disease can be detected.

In addition, in each of the above-described embodiments, the abnormal shadow of the lung is used as the second abnormal shadow, but the second abnormal shadow is not limited thereto. In the case of an abnormal shadow of a disease in which the first abnormal shadow and the second abnormal shadow are different from each other, in addition to the lung, the abnormal shadows of a disease of any part of the human body, such as the heart, the liver, the brain, and the limbs can be the second abnormal shadow. In this case, the learning model 23A of the second abnormal shadow detection unit 23 is trained using the supervised training data so that the abnormal shadow of the target disease can be detected.

Further, in the above embodiments, for example, as hardware structures of processing units that execute various kinds of processing, such as the information acquisition unit 21, the first abnormal shadow detection unit 22, the second abnormal shadow detection unit 23, the threshold value setting unit 24, the display control unit 25, the interpretation report creation unit 26, and the communication unit 27, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

What is claimed is:

1. A medical image processing apparatus comprising at least one processor,
    wherein the processor is configured to:
        acquire a first purpose of examination of a target medical image to be interpreted;
        set, according to the first purpose of the examination, a first detection threshold value or a first display threshold value for detecting a first abnormal region and a second detection threshold value or a second display threshold value for detecting a second abnormal region, wherein the first detection threshold value or the first display threshold value and the second detection threshold value or the second display threshold value are associated with the first purpose of examination;
        detect the first abnormal region from the target medical image by a first learning model which outputs a first detection result based on the first detection threshold value or the first display threshold value;
        detect the second abnormal region from the target medical image at a part different from a part including the first abnormal region by a second learning model which outputs a second detection result based on the second detection threshold value or the second display threshold value; and
        display the first detection result of the first abnormal region and the second detection result of the second abnormal region on a display.

2. The medical image processing apparatus according to claim 1, wherein the processor is configured to acquire the first purpose of the examination based on an operation history by an operator.

3. The medical image processing apparatus according to claim 2, wherein the operation history is a gradation condition set for interpretation of the target medical image.

4. The medical image processing apparatus according to claim 2, wherein the operation history is a display time of a part including the first abnormal region in the target medical image during interpretation before the detection of the first abnormal region from the target medical image.

5. The medical image processing apparatus according to claim 1, wherein the first abnormal region displays an abnormal shadow of a fracture.

6. The medical image processing apparatus according to claim 5, wherein a part of the fracture is a rib.

7. The medical image processing apparatus according to claim 1, wherein the processor is configured to:
    acquire a second purpose of examination of a target medical image to be interpreted;
    set, according to the second purpose of the examination, a third detection threshold value or a third display threshold value for detecting the first abnormal shadow and a fourth detection threshold or a fourth display threshold value for detecting the second abnormal region.

8. The medical image processing apparatus according to claim 1, wherein the target medical image is a three-dimensional image consisting of a plurality of tomographic images.

9. A medical image processing method implemented by a processor of a medical image processing apparatus, the method comprising:
    acquiring a first purpose of examination of a target medical image to be interpreted;
    setting, according to the first purpose of the examination, a first detection threshold value or a first display threshold value for detecting a first abnormal region and a second detection threshold value or a second display threshold value for detecting a second abnormal region, wherein the first detection threshold value or the first display threshold value and the second detection threshold value or the second display threshold value are associated with the first purpose of examination;
    detecting the first abnormal region from the target medical image by a first learning model which outputs a first detection result based on the first detection threshold value or the first display threshold value;

detecting the second abnormal region from the target medical image at a part different from a part including the first abnormal region by a second learning model which outputs a second detection result based on the second detection threshold value or the second display threshold value; and displaying the first detection result of the first abnormal region and the second detection result of the second abnormal region on a display.

10. A non-transitory computer-readable storage medium that stores a medical image processing program for causing a processor of a medical image processing apparatus to execute:

acquiring a first purpose of examination of a target medical image to be interpreted;

setting, according to the first purpose of the examination, a first detection threshold value or a first display threshold value for detecting a first abnormal region and a second detection threshold value or a second display threshold value for detecting a second abnormal region, wherein the first detection threshold value or the first display threshold value and the second detection threshold value or the second display threshold value are associated with the first purpose of examination;

detecting the first abnormal region from the target medical image by a first learning model which outputs a first detection result based on the first detection threshold value or the first display threshold value;

detecting the second abnormal region from the target medical image at a part different from a part including the first abnormal region by a second learning model which outputs a second detection result based on the second detection threshold value or the second display threshold value; and displaying the first detection result of the first abnormal region and the second detection result of the second abnormal region on a display.

* * * * *